US011416069B2

(12) United States Patent
Luo et al.

(10) Patent No.: US 11,416,069 B2
(45) Date of Patent: Aug. 16, 2022

(54) DEVICE AND SYSTEM FOR VOLUME VISUALIZATION AND INTERACTION IN A VIRTUAL REALITY OR AUGMENTED REALITY ENVIRONMENT

(71) Applicant: ImmersiveTouch, Inc., Chicago, IL (US)

(72) Inventors: Jia Luo, Chicago, IL (US); Jonathan Linsner, Chicago, IL (US); P. Pat Banerjee, Chicago, IL (US); Carter James Egan, Chicago, IL (US); Andrew Durnford, Chicago, IL (US)

(73) Assignee: ImmersiveTouch, Inc., Chicago, IL (US)

( * ) Notice: Subject to any disclaimer, the term of this patent is extended or adjusted under 35 U.S.C. 154(b) by 55 days.

(21) Appl. No.: 17/126,570

(22) Filed: Dec. 18, 2020

(65) Prior Publication Data

US 2021/0132687 A1    May 6, 2021

Related U.S. Application Data

(63) Continuation-in-part of application No. 16/839,803, filed on Apr. 3, 2020, now Pat. No. 10,872,460, which is a continuation-in-part of application No. 16/138,209, filed on Sep. 21, 2018, now Pat. No. 10,650,604.

(51) Int. Cl.
*G06T 19/20* (2011.01)
*G06F 3/01* (2006.01)
*G06T 15/08* (2011.01)

(52) U.S. Cl.
CPC .............. *G06F 3/012* (2013.01); *G06F 3/016* (2013.01); *G06T 15/08* (2013.01); *G06T 19/20* (2013.01); *G06T 2210/41* (2013.01); *G06T 2219/2008* (2013.01); *G06T 2219/2016* (2013.01)

(58) Field of Classification Search
None
See application file for complete search history.

(56) References Cited

U.S. PATENT DOCUMENTS

| 2008/0101667 | A1* | 5/2008 | Begelman .................. G06T 7/11 600/407 |
| 2014/0063054 | A1* | 3/2014 | Osterhout ............... G06F 3/005 345/633 |
| 2014/0088941 | A1 | 3/2014 | Banerjee et al. |
| 2016/0092645 | A1* | 3/2016 | Vlutters ................ G06F 3/0482 715/771 |
| 2017/0108930 | A1 | 4/2017 | Banerjee et al. |
| 2019/0026935 | A1 | 1/2019 | Podziemski et al. |

OTHER PUBLICATIONS

U.S. Appl. No. 17/126,570, filed Dec. 18, 2020, Pending.
U.S. Appl. No. 16/839,803, filed Apr. 3, 2020, Patented U.S. Pat. No. 10,872,460.
U.S. Appl. No. 16/138,209, filed Sep. 21, 2018, Patented U.S. Pat. No. 10,650,604.

(Continued)

*Primary Examiner* — Robert J Craddock
(74) *Attorney, Agent, or Firm* — DLA Piper LLP (US)

(57) ABSTRACT

The present technology relates to devices and systems for volume visualization and interaction in a virtual reality or augmented reality environment.

31 Claims, 6 Drawing Sheets

(56) References Cited

OTHER PUBLICATIONS

Ziegler, G., et al., "On-the-fly Point Clouds through Histogram Pyramids", Computer Graphics Stuhlsatzenhausweg 85, pp. 1-9.
Frieder, G., et al., "Back-to-Front Display of Voxel-Based Objects", pp. 1-9, IEEE (1985).
Pfister, H., et al., "Hardware-Accelerated Volume Rendering", pp. 1-16, The Visualization Handbook, (2005).
Volumetric Sort, Inigo Quilez, URL, http://iquilezles.org/www/articles/volumesort/volumesort.htm, downloaded on Mar. 28, 2019, pp. 1.
Vega-Higuera, F., et al., "High Performance Volume Splatting for Visualization of Neurovascular Data", pp. 271-278, IEEE Visualization (2005).
Orchard, J., et al., "Accelerated Splatting using a 3D Adjacency Data Structure", School of Computing Science, pp. 10, (2001).

* cited by examiner

DEVICE AND SYSTEM FOR VOLUME VISUALIZATION AND INTERACTION IN A VIRTUAL REALITY OR AUGMENTED REALITY ENVIRONMENT

CROSS-REFERENCE TO RELATED APPLICATION

This is a continuation-in-part of U.S. patent application Ser. No. 16/839,803 filed Apr. 3, 2020, which is a continuation-in-part of U.S. patent application Ser. No. 16/138,209 filed Sep. 21, 2018, now U.S. Pat. No. 10,650,604. The above-mentioned applications are incorporated herein by reference in their entirety.

FIELD OF THE INVENTION

The present technology relates to devices and systems for volume visualization and interaction in a virtual reality or augmented reality environment.

BACKGROUND

There is a need and desire for a tool that allows for quick loading of volume image data while also providing interactivity with the volume data, particularly in a virtual reality (VR) or augmented reality (AR) environment. Such a tool would be useful for medical diagnostic platforms using high resolution scanned image data (e.g., CT or MRI images).

BRIEF DESCRIPTION OF THE DRAWINGS

Specific examples have been chosen for purposes of illustration and description, and are shown in the accompanying drawings, forming a part of the specification.

DETAILED DESCRIPTION

The present technology relates to devices and systems for volume visualization and interaction in a virtual reality (VR) or augmented reality (AR) environment. The disclosed embodiments generally apply to volumes of all sources, including but not limited to medical imaging, industrial computed tomography scanning, three-dimensional mathematical modeling, three-dimensional scientific dataset, and the like. In a medical environment, the disclosed embodiments provide a tool for a doctor, physician or other medical technician to quickly load and review patient scans in a VR/AR environment. Moreover, unique and unobstructed views of the patient's scans are easily obtainable. The doctor, physician or technician may handle a scan as if it were a physical object in the palm of his/her hand, observing it from any angle to get the very best understanding of the situation at any zoom and detail level desired.

The disclosed embodiments generally apply to the presentation of one or multiple 3D medical imaging scans of all modalities, including but not limited to computed tomography (CT), magnetic resonance imaging (MRI), CT angiography (CTA), MR angiography (MRA), Cone Beam CT (CBCT), etc., and their post processing results. The disclosed embodiments generally apply to all medical specialties that utilize medical imaging, including but not limited to radiology, general surgery, craniomaxillofacial surgery, cardiothoracic surgery, neurosurgery, spine surgery, otorhinolaryngology, urology, etc.

The disclosed embodiments utilize geometric primitives referred to herein as "voxels", arranged in a "volume". It should be appreciated that the precise appearance or mathematical definition of voxels varies by application, and is not essential to practice the embodiments disclosed herein. These geometric primitives include that: each primitive may be uniquely identified by 3 integral coordinates (x,y,z); the (x,y,z) values of primitives' integral coordinates have a finite range; each primitive may be geometrically contained within a pyramid with a regular cuboidal bounding extent; the regular cuboidal bounding extents of no two primitives intersect in three dimensions; and the (x,y,z) lengths of the regular cuboidal bounding extents do not differ between any two primitives.

Figure 1:
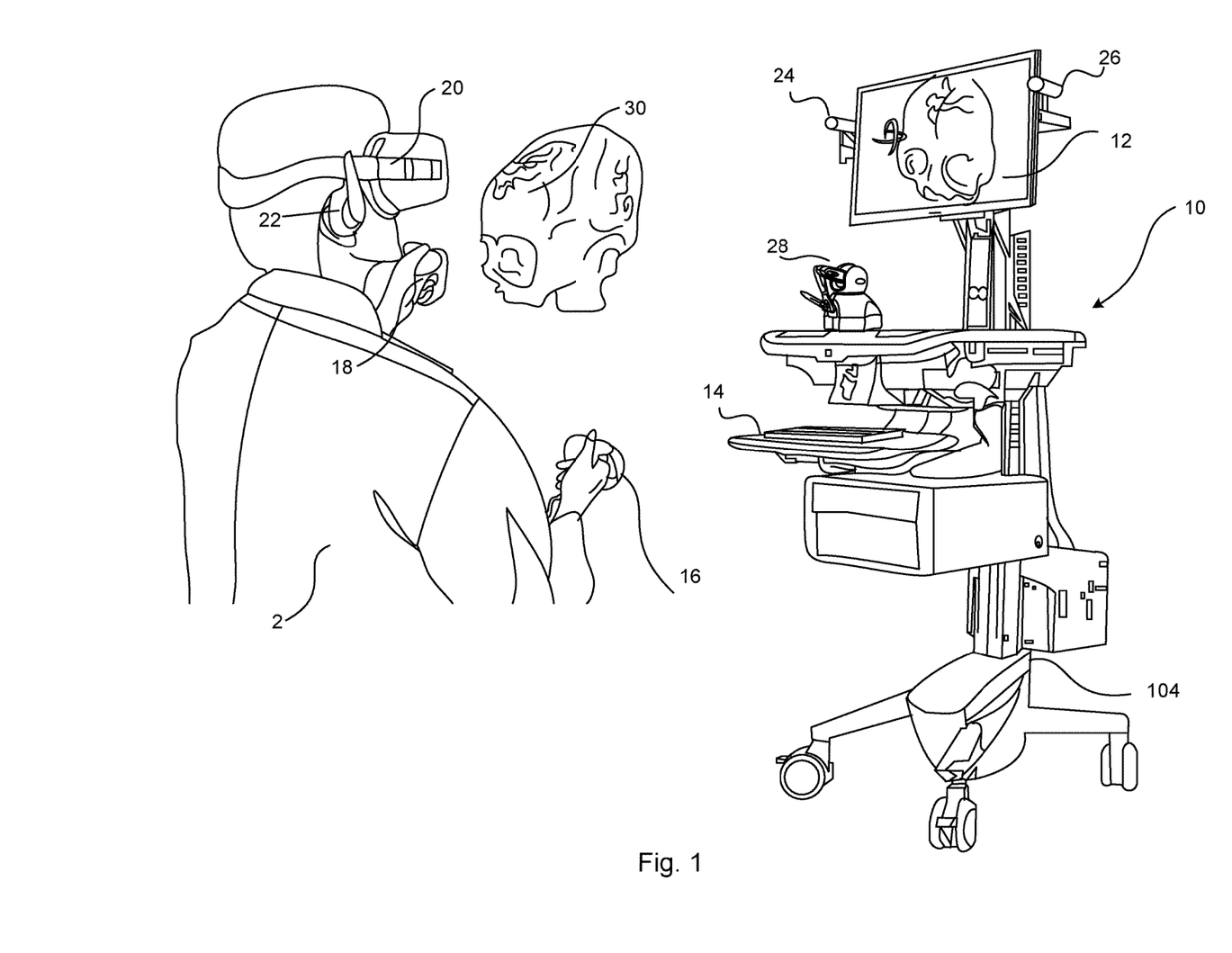
FIG. 1 illustrates one example of a portable workstation in accordance with the disclosed technology.
Figure 2:
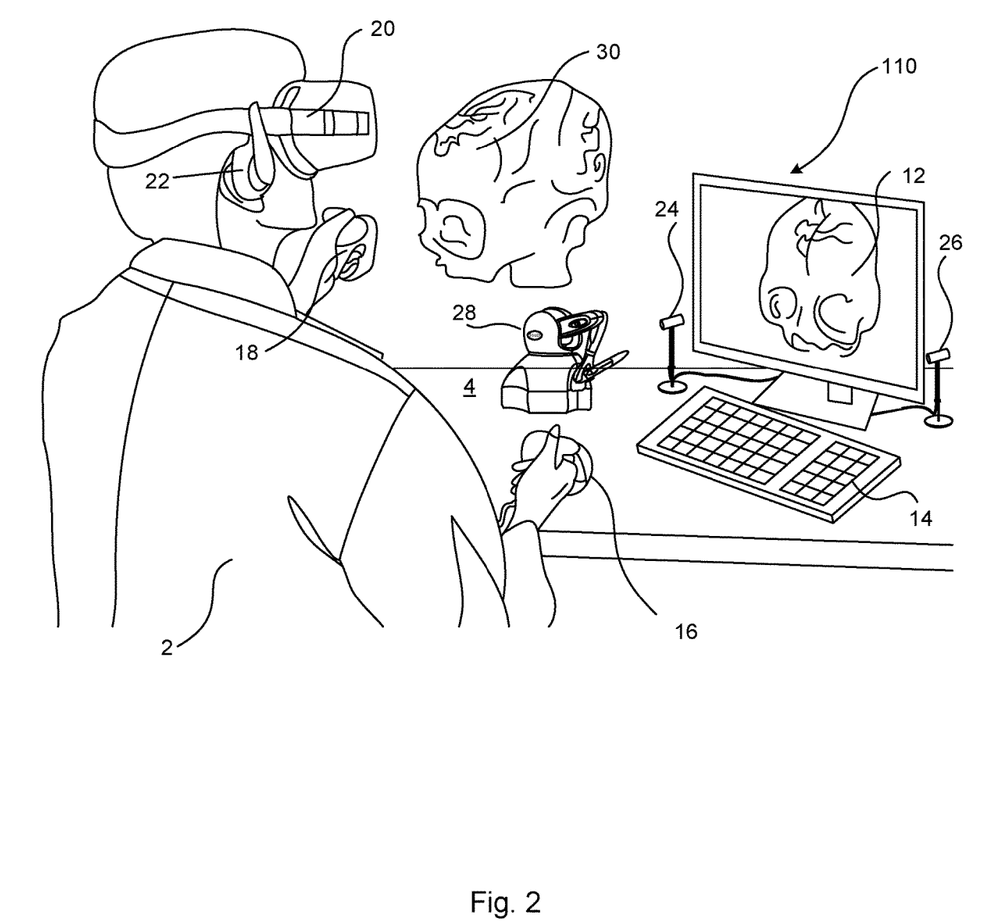
FIG. 2 illustrates one example of a workstation in accordance with the disclosed technology.

FIG. 1 illustrates one example of a portable workstation 10 in accordance with the disclosed technology while FIG. 2 illustrates one example of a workstation 110 in accordance with the disclosed technology. In the illustrated examples, the workstations 10, 110 include virtual or augmented reality devices and haptic devices, which along with the volume visualization and interaction discussed herein provide several advantages previously unattainable in the art. In one or more embodiments, the workstations may not include haptic devices. Thus, the disclosed principles and advantages over the current state of the art are obtainable on workstations 10, 110 that may not have haptic devices.

Referring to FIG. 1, the workstation 10 includes a display screen 12, keyboard 14 and a computer (not shown). The workstation 110 is shown being provided on a compact wheeled carrier 104, making the workstation 110 easily transportable (i.e., mobile/portable). The workstation 10 is shown being operated by a user 2. In the illustrated example, the user 2 is wearing VR/AR head mounted display 20 for viewing a virtual or augmented reality presentation 30 of volume data input into the workstation 10 and rendered by the workstation 10 in accordance with the disclosed principles. In the illustrated embodiment, a rendering of the volume data in accordance with the disclosed principles may also be presented on the display screen 12.

The user 2 is also shown wearing a headphone 22 for listening to auditory simulations as the user 2 observes and interacts with the volume data input into the workstation 10. In the illustrated example, the user 2 is operating two hand controllers 16, 18 also used to interact with the volume data rendered by the workstation 10 in accordance with the disclosed principles.

Referring to FIG. 2, the workstation 110 includes a display screen 12, keyboard 14 and a computer (not shown). The workstation 110 is shown being operated by the user 2 at a desk 4 or other works space. As explained below in more detail, due to the novel volume visualization and interaction provided by the disclosed principles, patient-specific data is easily loaded into, rendered and interacted with in both workstations 10, 110 making the workstations 10, 110 suitable for viewing critical scan information in all areas of e.g., a hospital (e.g., radiology labs, operating rooms, emergency rooms and even the doctors 'offices). The workstations 10, 110 may also be suitable for patient education and engagement. Patients may be able to better understand their condition and physicians may walk the patients through proposed interventions, actively consulting with them to determine the best therapeutic choice for their respective situations. This may reduce patient anxiety and reinforce the patients 'understanding of their treatment, and increase informed consent for medical plans of action.

Figure 3:
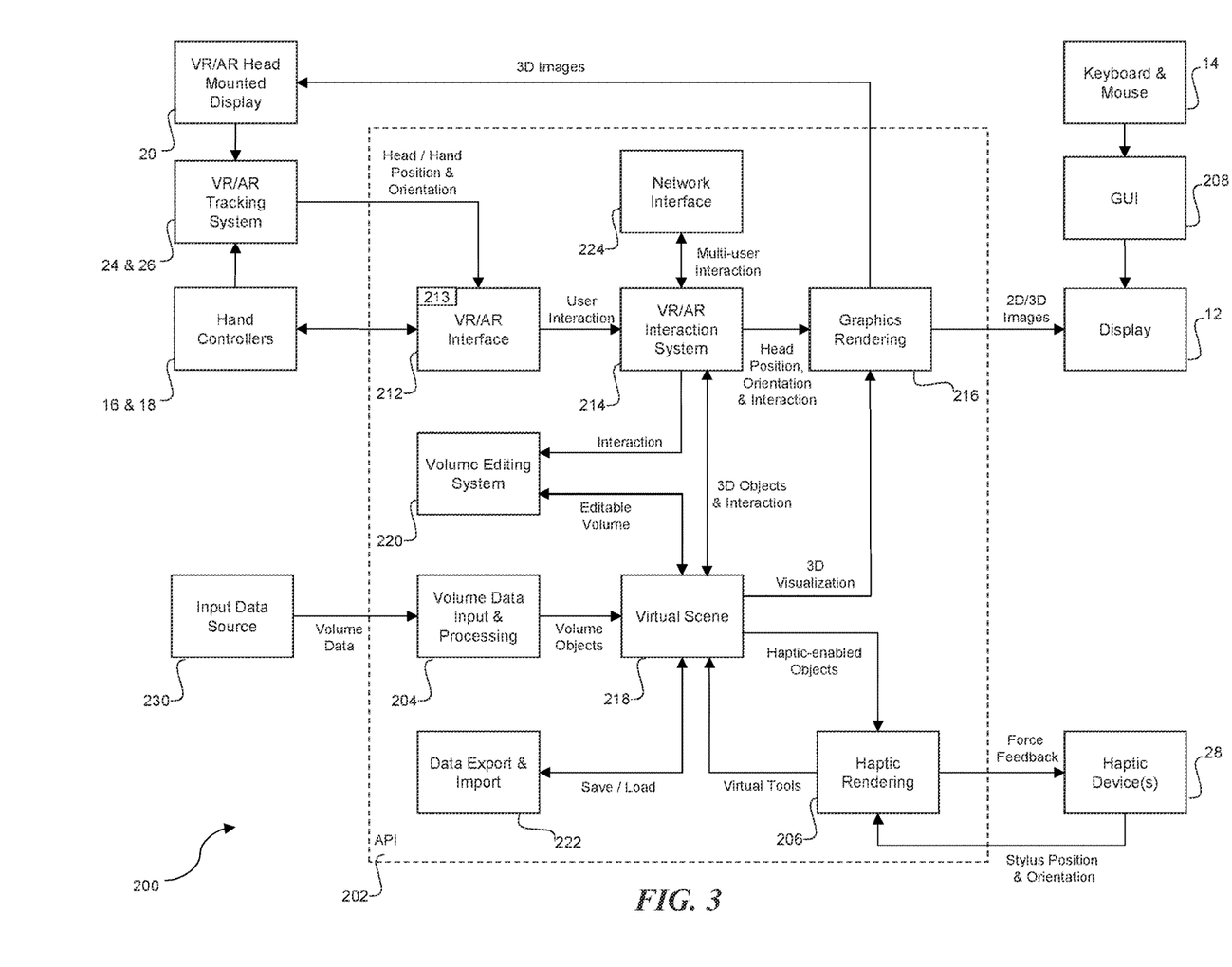
FIG. 3 illustrates a block diagram of a software and hardware architecture for the workstations illustrated in FIGS. 1 and 2.

FIG. 3 illustrates a block diagram of a software and hardware architecture 200 for the workstations illustrated in FIGS. 1 and 2. In the illustrated example, the architecture 200 includes interconnected devices and logic, which may be integrated by an application programming interface (API) 202. For example, the API 202 comprises a volume data input and processing block 204, which, among other things, may receive 3D image data, for example, generated by an input data source 230, which may be a medical scanner. The volume data input and processing block 204 may provide 3D volume objects to the virtual scene 218 as described in more detail below. Examples of medical scanners that may be used as an input data source 230 for characterizing physical objects include a magnetic resonance imaging (MRI) scanner or a CT scanner, such as those typically used for obtaining medical images.

The API 202 manages a virtual scene 218, which is a data structure that maintains all virtual objects, including but not limited to the imported volume data, the results of volume data processing, the surface representation of the volume objects, the virtual user interface and other objects introduced by the user interaction. The virtual scene 218 may be a tree structure with each virtual object being represented as a node. The logical relationships among the virtual objects is described by the tree structure, while the position, orientation and scale factor of each virtual object is defined by the transformation matrix associated with each node. A portion or the entirety of the virtual scene 218 can be saved or loaded via data exporting and importing block 222.

The API 202 may provide one or a plurality of camera nodes that compute the correct viewer-centered perspective projection on the virtual projection plane. It may properly render both left and right views according to the position and orientation of the user's head given by the tracking system.

In the illustrated embodiment, the API 202 may also include a virtual reality (VR)/augmented reality (AR) interface 212 for interfacing with virtual reality or augmented reality hardware, including VR/AR head mounted display 20 and hand controllers 16, 18 worn or operated by the user 2. The VR/AR interface 212 may include or may be connected to a wrist anchored user interface 213 and a VR/AR interaction system 214. As explained below in more detail various user interactions may be implemented and captured using the VR/AR interface 212, wrist anchored user interface 213 and VR/AR interaction system 214. The user's head/hand/wrist position and orientation and interaction data may be output from the VR/AR interaction system 214 in the illustrated embodiment.

The illustrated embodiment also includes a graphics rendering block 216, which receives inputs from several blocks, logic, etc. in the illustrated architecture 200. These inputs include volume objects, 3D objects, head/hand position and orientation, as well as user interaction data. 3D image data is sent to a display screen 12 and VR/AR head mounted display 20, and may be reproduced on graphical user interface (GUI) 208 presented on the display screen 12 or output to the VR/AR head mounted display 20.

In one or more embodiments in which haptic devices are being used, the API 202 may further include a haptic rendering block 206 for providing, among other things, force feedback to one or more haptic devices 28. The haptic device 28 is mechanical equipment that mediates communication between the user 2 and a computer and provides force output. The haptic rendering block 206 may monitor and control each haptic device 28, for example a stylus, or a plurality of styluses for different functions or for use by separate hands. The haptic rendering block 206 may link each haptic device 28 to a virtual tool in the virtual scene 218, and manage interactions between the virtual tools with haptic-enabled objects, including volume objects obtained from the volume data input and processing block 204.

In one or more embodiments in which haptic devices are being used, the graphics and haptics may be on two separate threads. The haptics and graphics may have distinct update schedules; for example, haptics at 1000 Hz and graphics at 90 Hz. In this example, the system may synchronize the two consecutive graphics updates after approximately every 30 haptic updates, and it is within the skill of artisans to modify the manner in which haptics and graphics update and synchronize.

In the illustrated embodiment, the API 202 also includes a volume editing system 220, which edits one or more volume objects maintained in the virtual scene 218 based on user interactions from VR/AR interaction system 214. The edible volume objects and their surface representation may be modified in real-time, or separated into multiple independent segments.

The illustrated embodiment also includes a network interface block 224, which sends multi-user interaction data from VR/AR interaction system 214 to other users on the network, and also receives interaction data from other users.

The architecture 200 has been described generally. Further details of the various aspects of the architecture 200 are now provided.

The volume data input and processing block 204 may input volume data supplied in either DICOM or MetaImage formats. Volume data with 16-bit and 8-bit integer values may be directly supported; other formats may be automatically converted to 16-bit. To accommodate various types of input data sources, the volume data contents of scalar images (such as CT or MRI) and segmented objects may be both supported by the volume data input and processing block 204.

In case more than one volume data is imported, the volume data input and processing block 204 may implement a coregistration process which aids in aligning (coregistering) multiple scans, potentially of different modalities. The coregistration represents pairwise proper rigid transforms between the coordinate spaces of the scans. The scans are presented both in a traditional axial-sagittal-coronal 2D format, and as overlaid maximum intensity projection (MIP) 3D visualizations. The coregistration may be performed manually via mouse and keyboard controls, or semi-automatically via a partial Procrustes superimposition of user designated feature points paired between the scans. The resulting transformation matrix shall be applied to the related volume objects and all associated layers.

The volume data input and processing block 204 may implement a volume meshing process which generates surface geometry from iso-surfaces across the volume objects while sufficiently performant as to allow constant real-time alterations of surfaces. Based on surface nets algorithms, it may be able to infer and generate a variety of sub-voxel geometric features from the trilinear interpolation function, including the disambiguation of what would otherwise be non-manifold portions of the surface. This is particularly evident in the visualization of thin or tunnel-like structures such as the foramina. Surface normals are also generated for use in lighted rendering, in such a way as to automatically produce an appropriate mixture of hard edges and curved surfaces to satisfyingly represent complex edges without the appearance of undue darkness or obvious facets.

The volume data input and processing block 204 may also implement a topological smoothing process intended to be used in combination with the volume meshing process, which produces a smoother mesh from a volume object of binary segmentation without overly deviating from the original geometry. Because the topological smoothing process takes place before regular meshing, the smoothed mesh and scalar data are self-consistent, and the system's output is fully and transparently compatible with any volume-manipulating features, and can be trivially converted back into the original binary segmentation. The smoothing computation takes place partially on the GPU.

The volume data input and processing block 204 may also implement a series of post processing algorithms of noise reduction to improve the visual fidelity of volume visualization. The edge and feature preserving smoothing algorithm may be executed upon volume objects to suppress low-amplitude noise across all frequencies, and make voxels of same material cluster closer in scalar value. Upon the output of the smoothing algorithm, an algorithm of small isolates culling may be executed which removes additional noise by replacing topologically isolated small fragments within the volume object with smooth data. Upon the output of the small isolates culling algorithm, a deconvolution algorithm may be executed which simultaneously hardens edges and smooths where no edge exists. Thus, the influence of the point-spread function is removed, voxels of the same material cluster closer together in scalar value, and remaining fragments of noise become more topologically isolated. Upon the output of the deconvolution algorithm, the small isolates culling algorithm may be executed again—thus, some topologically isolated small fragments that were not identified in the first execution of the algorithm may be replaced with smooth data.

According to the disclosed principles, a number of segmented volume objects produced from the same source volume object may optionally be recombined into a single volume object having auxiliary layer ID voxels. The layer ID may be used to simulate a single object consisting of distinct, interconnected materials. In addition to, or alternatively, segmented volume objects may be cropped to the Axis-Aligned Bounding Box (AABB) containing existent voxels, while retaining position information. In addition to, or alternatively, a number of segmented volume objects produced from the same source volume object may be individually cropped to the AABB of the union of their existent voxels. In one embodiment, segmented volume objects are converted to scalar volume objects via a topological smoothing process.

The volume data input and processing block 204 may also implement volume ray casting, which may effectively and accurately calculate the first intersection point of a given ray and a given iso-surface of the volume object. This functionality facilitates other volume operations including ray casting and collision detection.

The data export and import block 222 may implement scene exporting and importing processes. The scene exporting process may save the entirety of the virtual scene 218 of the active session, including the original, processed or edited volume object, its surface representation, as well as the results of user interaction, as external files. The scene importing process may load and recover the virtual scene 218 from a previously saved session. In a desired embodiment, the exported data may be saved in a portfolio of files with unique file extension, so the importing process can identify the files by such file extension.

The data export and import block 222 may also implement a model exporting process, which converts the surface representation of the original, processed and/or edited volume object into polygon mesh models, and save them into the file system. In one embodiment, the exported models may be saved as STL files or OBJ files.

The graphics rendering block 216 may implement a variety of visualizations of the volume data either on 2D planes and/or in 3D space, including but not limited to Shaded Surface Display (SSD), Volume Rendering Technique (VRT), Multi-Planar Reformation (MPR), Maximum Intensity Projection (MIP), and Minimum Intensity Projection (MinIP).

In one embodiment, the graphics rendering block 216 may implement the visualization via shaded surface display (SSD) which reflects structures of interests by visualizing the surface representation of volume layers generated by the volume meshing process. A volume layer is a set of geometry that shares the same rendering material and source. It can be either constructed from an iso-surface contained in a scalar volume object, or from a binary volume object derived from segmentation. Multiple iso-surface layers can be created from the same volume object.

The graphics rendering block 216 may also implement an Order-Independent Transparency (OIT) method which may be used to render arbitrary unsorted polygons with correctly sorted transparency. This allows displaying multiple volume layers with adjustable and correct transparency. In a desired embodiment, the OIT method is implemented using the A-Buffer technique with a per-pixel linked list. As the anatomy is being rendered, the fragments are accumulated in these lists instead of directly composited to the frame buffer. At the end of the frame, the lists are sorted by depth, blended, and then composited with the opaque parts of the scene.

The rendering of layers as geometry allows seamless multi-modality rendering. Segmentations or iso-surface layers can be mixed and matched from different scan modalities. Applying the OIT method, the opacity of each layer can be adjusted independently from fully opaque to fully hidden or anywhere in between. Layers from every loaded medical imaging datasets faithfully represent the patient specific anatomy in virtual reality; they can also be accurately superimposed with the actual patient in an augmented or mixed reality environment. As a volume object is modified, its associated mesh may be updated in real-time.

It should be appreciated that a number of rendering features may be available. At both design time and runtime, rendering features may be toggled on or off, or have their parameters changed. These features may include, but are not limited to, per-layer colors, diagrammatic cutaways, soft deformation in response to touch, and X-ray visual simulation. In one embodiment, two lighting options may be available: a point light without distance attenuation attached to the camera, and an image-based lighting scheme with directional occlusion. In addition, the meshes may be exported for use in external software.

The display outputs, from both the 3D and 2D renderings, may be presented on both the VR/AR head mounted displays 20, and the regular computer displays 12 like monitors, projectors or televisions. To generate display outputs on the VR/AR head mounted displays 20, two scene cameras are set to move and rotate based on the positions and orientations of both eyes of the user, which is obtained from the VR/AR tracking system 24, 26. Stereoscopic vision and depth perception are therefore achieved via the difference of the display outputs for both eyes. On regular computer displays 12, the display output can either be the clone of one of the outputs to the VR/AR head mounted displays 20; optionally, for better experience of the surrounding audiences observing the volume visualization and interaction with the user 2 via regular computer displays 12, the output can be obtained from a separated scene camera which follows the perspective of the user 2 while keeping the camera movement smooth and steady.

Figure 4:
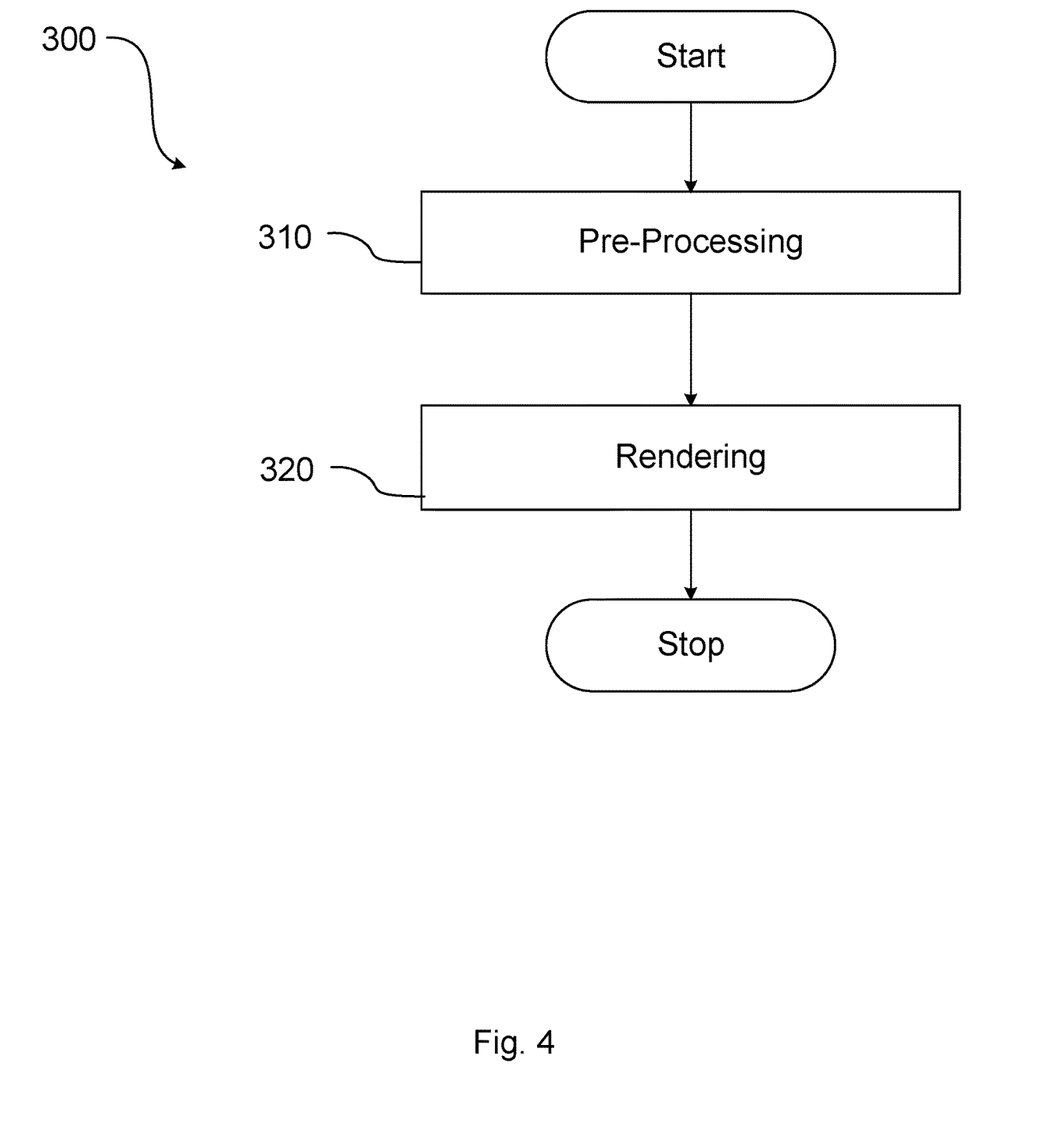
FIG. 4 illustrates a process according to a disclosed embodiment.

In a desired embodiment, a volume object may be visualized with a novel rendering technique referred to herein as a view-ray-ordered volume rendering technique (for the graphics processing unit discussed below). For visualization of end-user provided volume data, the workflow may be as follows: First, unnecessary structures are eliminated. To do so, the user 2 outlines a 2D region of interest on a maximum intensity projection image of the volume data about any voxel-aligned axis. This 2D region is projected into a 3D polyhedron constrained by the AABB of the volume object, and any information outside of the 3D polyhedron is discarded. Next, a transfer function is specified, aided by an interactive 3D visualization using process 300. The transfer function includes an isovalue defining the iso-surface of interest, as selected on a data value histogram of the volume object. The transfer function furthermore includes scale and bias values that modulate a gradient magnitude driven color ramp. The color ramp tends to distinguish softer versus harder materials. Finally, opacities corresponding to the two extrema of the color ramp may be modified, and rendered with exact transparency. All transfer function changes reflect immediately on the 3D rendering. Details are rendered with sub-voxel interpolated detail.

The graphics rendering block 216 may also implement the direct volume ray-caster, which renders multiple iso-surfaces or a signed distance fields obtained from the volume data by marching a ray though the volume object and evaluating intersections with the surfaces. It supports multiple iso-surfaces at different scalar values, with correct transparency, and optionally participating medium rendering. Participating medium rendering simulates increasing opacity as the material gets thicker. Each surface can have different material settings, which may include but not limited to color, opacity, and density for the internal material.

The graphics rendering block 216 may also implement the rendering of multi-planar reconstruction (MPR) of the volume object on an intersecting 2D plane. The scalar value at each pixel of the plane can be determined by trilinear interpolation of the voxel values of the containing voxel cell in the volume grid. The MPR can be rendered in greyscale or pseudo-color with fully configurable mapping of the colors with the voxel values. Transparency can be set along with the color mapping to allow viewing of the 3D rendering behind the MPR overlay, or making certain portion, such as the space outside of the region of interest, less noticeable or even invisible.

As discussed above, in one or more embodiments in which haptic devices are being used, the haptic rendering block 206 may allow interactions between a virtual tool corresponding to the haptic device 28 and objects within the virtual scene 218. A haptic proxy is maintained to describe the position of the haptic interface point, which tends to move towards the actual position of the haptic stylus, but always stays outside any haptic-enabled objects. Each object may be assigned different haptic materials, according to certain parameters: stiffness, viscosity, static friction and dynamic friction, as well as different physical properties such as density, mass, thickness, damping, etc. Therefore, the user 2 may perceive different surfaces and textures when touching the haptic-enabled objects.

In one or more embodiments in which haptic devices are being used, the haptic rendering block 206 may track events of haptic interaction, including the beginning of contact, end of contact, continuous contact, penetration, to name a few. Custom behavior may be programmed when the events are triggered. The haptic-enabled objects may be configured to be penetrable, and the objects may be considered to be penetrated through when the magnitude of the proxy offset exceeds a predetermined/specific threshold.

In one or more embodiments in which haptic devices are being used, the haptic rendering block 206 may implement spatial constraints of the haptic interaction point, which limit the degrees of freedom of the translation and/or rotation of the virtual stylus. The haptic rendering block may also implement programmable custom haptic force effects, such as constant force, gravity, viscosity, vibration, magnetic effect, to name a few.

In one or more embodiments in which haptic devices are being used, the architecture 200 may support, via the haptic rendering block 206, volume haptics interaction, which may allow a haptic device 28 to present tactile feedback of volume objects. The haptic rendering block 206 enables haptic interaction of any number of volume objects, with one layer per volume object. For each volume object, a subset of voxels near the moving path of the haptic proxy may be collected. An iso-surface within this subset of voxels may be computed, and used to determine a new position for the haptic proxy. Multiple iterations of this process may be executed within a frame to refine the proxy position. A force proportional to the offset between haptic proxy and the actual stylus position may be output to the haptic device 28 as the tactile feedback of the volume object.

In accordance with the disclosed principles, and in one or more embodiments in which haptic devices are being used, volume haptic interaction may be compatible with haptic rendering of polygon mesh objects in the same virtual scene 218. Volume haptics interaction may also work with non-static volume objects, whose voxel data may be modified in run time to simulate the change of geometry such as drilling, cutting, etc.

In accordance with the disclosed principles, the VR/AR interface 212 may be designed and implemented to provide compatibility with various virtual reality or augmented reality hardware. Specifically, the VR/AR interface 212 may identify active virtual reality or augmented reality hardware (i.e., VR/AR head mounted display 20 and hand controllers 16, 18) upon startup of the disclosed workstations 10, 110, and may map the correct inputs and outputs for the head mounted display 20 and hand controllers 16, 18 being used. In a desired embodiment, world-based user interfaces and custom build hand models may be implemented into the architecture 200 such that each user may receive a consistent experience even though different VR/AR head mounted displays 20 or hand controllers 16, 18 are being used. The VR/AR interface 212 may support dominant and secondary hand references, allowing the architecture 200 to switch from right-handed mode to left-handed mode at any time. In the disclosed embodiment, the user's hands may track any volume object via distance tracking. The tracking needs not be dependent on any collision bounds, allowing for more accurate interaction with small objects that are in close proximity.

In a desired embodiment, the VR/AR interface 212 includes the wrist anchored user interface 213 designed specifically for being used in conjunction with volume objects in accordance with the disclosed principles. Being anchored to the wrist may allow the volume objects to be scaled many times its original size, as well as letting the user 2 travel inside the volume layers. Icons and tags of the UI buttons may be rendered in a depth-independent manner, allowing the user 2 to see the buttons even when standing inside a solid volume layer. The UI may also easily be moved out of the way for viewing.

As noted above, the API 202 also includes the VR/AR interaction system 214. The VR/AR interaction system 214 may provide one or more of the following features useful for volume visualization and interaction in accordance with the disclosed principles: 1) spatial tracking; 2) grab manipulation; 3) measurements; 4) snapshots; 5) visual configuration; 6) cutaway and 2D overlay; 7) drawing; 8) hardware placement; 9) laser pointer; 10) multi-volume comparison; 11) multi-user collaboration and/or 12) undo-redo. Each feature is described below.

Spatial tracking may allow high precision tracking of objects in the virtual scene 218. For any tracking subject, which is typically associated with virtual reality or augmented reality hardware (i.e., hand controllers 16, 18 or VR/AR head mounted display 20), the distance to any tracked object can be calculated to help the VR/AR interaction system 214 execute the interaction features and specify the virtual object being interacted by the user 2. Events can be associated to each tracked object and they can be automatically triggered if the distance to the tracking subjects meets the predefined criteria.

When a tracking request is made, the distance can be interpreted by a plurality of mechanisms, including but not limited to the signed distance function, the global signed distance field, or the closest point searching. The signed distance function is a mathematical function which defines a geometric primitive, or a union of multiple primitives and calculates the distance to any given point in 3D space. It may define or approximate the tracking distance of the geometry of any object in the virtual scene 218. The sign of the output distance may describe if the tracking subject is inside or outside of the tracked objects. For any volume layer in the virtual scene 218, a global signed distance field can be computed to aid in accurate tracking. The nearest position on a volume layer is estimated using the gradient of the signed distance field as a direction to project that distance. If a tracking request occurs for a subject outside the volume grid, the nearest point on the boundary of the volume grid is used to locate the nearest position on the surface. For any objects that can be represented or approximated by a collection of points, such as polygon meshes with dense vertices, the tracking distance can be determined by searching the point closest to the tracking subject, and calculating the distance to such point.

In accordance with the disclosed principles, the manipulation feature may allow the user 2 to intuitively grab and manipulate a volume object in lifelike way. This feature may allow the user 2 to seamlessly explore the volume object externally and internally. Using triggers or buttons on hand controllers 16, 18 as well as position and orientation of the hands obtained from VR/AR tracking system 24, 26, the volume object may be translated, rotated or scaled in 3D space. For example, when one hand squeezing the trigger, the volume object can be freely moved and orientated; when two hands grab an empty space, the volume object may rotate and scale around its own axis; when two hands grab inside the volume object, the volume object may be pivoted to both hands, and move, rotate and scale with regards to the movement of the hands.

In one or more desired embodiments, the degree of freedom (DoF) of manipulation may be constrained so the translation along one or more axis, and/or the rotation around one or more axis may be limited or even locked. The rotational pivot may also be customized.

The measurements feature may provide accurate 3D measurements of a plurality of spatial properties based on the source dataset. The user 2 may measure the distance between two points, the cumulative length of a polygonal chain, the angle between two lines, the angle between two planes, the circumference of a circle, the volumetric size of a user defined space, and the volumetric size within an iso-surface. The measurements feature may also include a snap-to-volume feature that may find the closest point on the surface of the volume layer to correct the user's placement. As can be appreciated, this may increase accuracy of the point placement, thus increasing measurement accuracy.

The snapshots feature is a tool that may allow the user 2 to capture a static picture of the virtual scene 218 from a user specified perspective at a user defined time. One embodiment may allow the snapshots to be saved as "PNG" files. The user 2 may look through a physical frame to help focus on the virtual scene 218 to be captured. Once a snapshot is taken, a preview may be displayed on the VR/AR interface 212, and the image may be saved to an external folder. The user 2 may switch between portrait and landscape modes as desired.

The visual configuration feature may provide real-time adjustment of the visual properties of different volume objects. These visual properties include but not limited to colors, level of transparency, isovalues, transfer functions, special visual effects achieved by shaders, etc. The graphic rendering block 216 may update the rendering of the volume objects to reflect any changes of visual configuration.

The cutaway and 2D overlay feature may allow user 2 to specify one or multiple adjustable 2D planes across the 3D rendering of the volume object. It is optional to render the multi-planar reconstruction (MPR) of a source volume object or the fusion of multiple volume objects on any planes. If more than one volume objects exist, different planes may render the MPR of the same or different volume objects. The planes can be in axial, coronal, sagittal, or any arbitrary orientations. Optionally, the 3D rendering on either side of any plane can be diagrammatic culled out in order to view the internal structure, or view the entire MPR overlay. The graphics rendering block 216 may update both the 3D rendering and the 2D MPR rendering in real-time based on user interaction.

The drawing feature may allow the user 2 to draw in the virtual scene 218. In a desired embodiment, the tip of the drawing tool may be kept on the surface of one or more volume layers and/or 3D objects in the virtual scene 218. The drawing feature may also include an option to measure the accumulated length of the curves drawn by the user 2.

The hardware placement feature may introduce one or more of the 3D objects to the virtual scene 218. These 3D objects can be independently included in the virtual scene 218, or mounted to any volume object in the virtual scene 218. In case the 3D objects overlap with the volume layers, the level of overlapping may be measured, and the objects may be rendered with a color gradient representing the depth of intersection. In one or more embodiments in which the system is implemented for one or more of surgical planning, patient engagement and/or medical education, the 3D objects may be models of medical implants, surgical plates and screws or surgical instruments, which are originally displayed on the wrist anchored user interface 213 and can be added into the virtual scene 218 and attached to any volume object. In a desired embodiment, the surgical plates may be automatically bent against the surface of one or more volume layers so it fits the curvature of the anatomy structure.

The laser pointer feature may allow the user 2 to point out specific positions and features on a volume object for the benefit of the viewing audience. The point where the laser comes in contact with the volume object may be calculated by ray casting algorithm, and the point may be visually highlighted to help draw attention to the point of interest.

The multi-volume comparison feature may allow the user 2 to view multiple volume objects in the same virtual scene 218, and compare the volume objects side by side. In one embodiment, one volume object may be put on top of another one so that the volume objects may snap to the same position, allowing an overlaid comparison. In another embodiment, the volume object can be compared with the lateral inversion of itself, highlighting the symmetric differences.

The multi-user collaboration feature may allow multiple users to share the virtual scene, and interact with the same volume objects. All users may be able to manipulate and edit the volume objects, and see the changes applied locally. In one embodiment, a voice/chat feature may be provided to allow users to communicate directly. The connection may be over local networks and/or over a wide area network such as the internet.

The undo-redo feature may allow the user 2 to undo interactive operations and recover the virtual scene 218, including the volume objects, their corresponding surface representation, and other 3D objects, at a previous state; or reverse the undo operation and recover the virtual scene 218 at a state prior to the undo operation. Features and operations in the VR/AR interaction system 214 are implemented by performing a number of low level operations on objects in the virtual scene 218. In order to group low level operations into a single logical high level operation, all tools perform the operations on a context object which may be first acquired from the API 202. This also serves as a locking mechanism to prevent multiple tools from modifying the volume objects in unpredictable ways.

Each low level operation may be implemented as a command object that records the before and after states of its execution. When a tool performs operations, the context records a list of all the commands that have been executed by the current tool. When the tool is finished making changes, it releases the context to finalize its changes. The context bundles the low level operations into a single high level undo-redo operation so that when the user 2 triggers the undo feature, all of the changes made by the last tool will be reverted, even if they consist of multiple subcommands. Once the high level undo-redo command is assembled, it is added to a linked list of previous undo-redo commands. Operations may be undone and redone by applying the appropriate state from each command. The undo-redo queue can also be serialized to disk, both to support resuming a session, but additionally as a record of all the steps taken in the planning session.

As noted above, the API 202 also includes the volume editing system 220, which allows one or more editable volume objects and their surface representation to be modified in real-time, or separated into multiple independent segments. The volume editing system 220 may implement a volume cutting feature, which allows the user 2 to cut one or more volume objects and their surface representation. When user 2 confirms the cuts, the editable volume objects is then modified so their surface representation matches the cuts, and additional volume objects may be generated to represent the newly cut partitions. The volume editing system 220 may also implement a volume sculpting feature which allows the user 2 to frequently modify one or more volume objects and their surface representation in the region specified by the user 2, in order to gradually remove materials from the represented geometry, or add materials to it. The area being edited may be specified by either a signed distance function (SDF) or a connected component labeling (CCL) process.

The signed distance function (SDF) is a mathematical function that can return a signed distance from the cut boundary to any point in the volume object. The SDF may include but is not limited to a plane, geometric primitives including cuboid or sphere, or a manifold mesh. The editing modifies the original volume object to reflect the remaining part, and if needed, generates additional volume objects for the newly cut segments. The region of interest for the editing, which is conservatively defined as any cuboidal area that could contain all voxels being modified, may define the size and dimension of the new volume objects. The voxel values from that area are copied from the original volume data. To construct the cut hollow surface in the original volume object and the solid surface in the new ones, the signed distance function shall be applied to every voxels in the region of interest in the original volume object, and then applied in the new volume objects but with the distance sign reversed. The new signed distance value at any voxel shall be the minimum of the original value and the distance returned from the function.

In a desired embodiment, user may define one or more SDFs through auxiliary 3D shapes introduced in the virtual scene 218. In another desired embodiment, user 2 may define the area to be edited by gradually painting on the editable volume objects through VR/AR interaction system 214, by a virtual paint bush of various shapes and dimensions, and the area to be separated may be rendered with highlighting visual effects.

The connected component labeling (CCL) may be a process which uniquely labels all subsets of the voxels whose represented geometries are connected. The volume editing may be achieved by breaking such connectivity with one or multiple mesh based cutting boundaries defined by the user 2. In a desired embodiment, the editable volume objects may be automatically separated into independent partitions by the CCL process. In another desired embodiment, the CCL process may detect whether a cut specified by user 2 may successfully separate one or more editable volume objects, and the forecast of the cutting results may be presented to the user 2 before the cut is finalized.

One or multiple new volume objects may be generated to describe the newly separated subsets of voxels, with the voxel values copied from the origin volume object. To construct the cut surfaces of both original and new volume objects resulted from user defined boundaries, the values of the voxels in all voxel cells that intersect with the boundary mesh shall be modified according to the minimum distance between the voxel and the mesh.

To update the 3D rendering of the volume objects, volume meshing shall be reexecuted once volume editing is completed. The user 2 may have multiple options to interact with the newly generated volume objects. These interaction features may include removal, manipulation, and various measurements.

FIG. 4 illustrates a process 300 according to a disclosed embodiment. As discussed above, the process 300 is a view-ray-ordered volume rendering technique for a graphics processing unit (GPU). It is well known that volume rendering is a computationally expensive operation. Medical images can contain hundreds of millions of voxels. Thus, it may be desirable to restrict rendering to only the interesting voxels; however, even one iso-surface of interest within a medical image may easily include tens of millions of voxels. Furthermore, for many applications, it may not be sufficient to render the outermost visible surface of an object embedded in a volume. Numerous transparent elements may be visible throughout a volume. This may prohibit the simple Z-buffering technique.

At the same time, display resolutions and frame rate expectations are climbing, which further exacerbate the difficulties of volume rendering. Typical volume rendering techniques support interactive rates of approximately 10 Hz, usually restricted to a small viewport in a desktop application. On the other hand, modern users demand virtual and or augmented reality experiences, which may run at the frame rate of up to 90 Hz with render resolutions upwards of 5 million pixels. The render resolution required for virtual or augmented reality rendering climbs higher every year. Under these circumstances, volume rendering may present an extreme computational burden that may only be met by the graphics processing unit (GPU).

The inventors acknowledge that a large body of work exists on volume rendering. Broadly, these are classified as image-order or object-order techniques. Image-order techniques trace a ray or a cone through the volume for every pixel on the imaging plane. This is described e.g., in Hanspeter Pfister, Hardware-accelerated volume rendering, in C. D. Hansen and C. R. Johnson, editors, The Visualization Handbook, pp. 229-258 (Elsevier, 2005) (https://pdfs.semanticscholar.org/1015/b715cb220aa0b22aa11bd7a4bd5b25104ae3.pdf) (hereinafter "Hanspeter Pfister"). While many techniques for accelerating these ray-traces exist, volume ray-tracing scales poorly with increasing resolution. Small stepping of rays leads to good locality of the reference, but the exhaustive sampling of the volume across many pixels is inefficient. Large stepping of rays via empty-space-skipping techniques alleviates the burden of sampling, but introduces locality of reference problems, which also results in inefficiency (particularly for complex volumes). Image-order techniques predominate due to their simplicity of implementation, but they do not suit real-time, high-resolution applications.

Object-order techniques, on the other hand, draw volume elements onto the imaging plane. One technique is known as volume slicing, whereby a volume is rendered via an ordered stack of textured quads. This is also described in Hanspeter Pfister. While possessing some good properties, such as high locality of reference and good utilization of hardware interpolation, volume slicing is an exhaustive sampling of every voxel in a volume. Thus, it only scales to very small volumes. Furthermore, slicing exhibits serious rendering artifacts.

The other major object-order technique is volume splatting, whereby each voxel is independently drawn onto the imaging plane. Described in Hanspeter Pfister. A central consideration of splatting is how to draw the voxels in order, so that they composite together correctly. Existing techniques include exhaustive Painter's Algorithm rendering from a dense 3D array, as described e.g., in Back-to-Front Display of Voxel-Based Objects, Gideon Frieder, Dan Gordon, R. Anthony Reynolds (http://www.codersnotes.com/notes/euclideon-explained/voxel-btf.pdf), pre-sorting for one or more view directions on the CPU, as described e.g., in High Performance Volume Splatting for Visualization of Neurovascular Data, F. Vega-Higuera*P. Hastreiter R. Fahlbusch G. Greiner § Neurocenter, Dept. of Neurosurgery and Computer Graphics Group University of Erlangen, Germany (https://pdfs.semanticscholar.org/1959/b18e5a59bedc2ba79200d5d70734dbd8126f.pdf), Volumetric Sort, Inigo Quilez (http://iquilezles.org/www/articles/volumesort/volumesort.htm) (hereinafter "Volumetric Sort"), or extracting a voxel order from a multidirectional run-length encoding format as described e.g., in Accelerated Splatting using a 3D Adjacency Data Structure, Jeff Orchard, Torsten Möller School of Computing Science Simon Fraser University, Burnaby, British Columbia, Canada (https://eprints.cs.univie.ac.at/5040/1/2001_-_Accelerated_Splatting.pdf). All existing techniques are fundamentally sequential and CPU-bound.

Unlike the image-order and object-order techniques, and unique solely to the process 300 disclosed herein, is the manner in which the GPU is used to draw the voxels in view order, from a compressed representation of the voxel coordinates. The coordinate compression keeps memory consumption and bandwidth usage low. High locality of the reference is maintained through all stages of the algorithm.

As will be discussed below in more detail, the process 300 comprises a pre-processing stage 310 followed by a rendering stage 320. In the pre-processing stage 310, each voxel possibly existent within the coordinate range of the volume object must undergo a binary classification as existent or nonexistent; i.e., to be rendered or not rendered, respectively. The details of this classification are application-dependent and not essential to practice the principles disclosed herein. However, the process 300 performs an amount of work proportional to the number of existent voxels (until the final rasterization stage). Thus, the process 300 requires the binary classification as an input. The classification is either created as, or transformed to, a binary mask volume.

In one embodiment, the binary mask volume is transformed into a HistoPyramid such as one described e.g., in On-the-fly Point Clouds through Histogram Pyramids arbrücken, Germany Gernot Ziegler, Art Tevs, Christian Theobalt, Hans-Peter Seidel Max Planck Institute for Informatics, Computer Graphics Stuhlsatzenhausweg 85, D-66121 Saarbruecken, Germany (https://pdfs.semanticscholar.org/35e3/3e7752a721289ec2c8599409db0d56693f77.pdf). In the disclosed embodiment, the HistoPyramid is a hierarchical grid of element counts per grid cell. The original binary mask volume is retained to comprise the leaves of the HistoPyramid.

Each existent voxel may be logically assigned an index according to some fixed and particular (but arbitrary) traversal order of the HistoPyramid, henceforth the "fixed order." Voxel indices range from 0 to the number of existent voxels.

A look-up table may be created that maps high-order bits of voxel coordinates to high-order bits of voxels 'fixed order (i.e., via a prefix sum). Exactly how many bits are mapped is an implementation detail that is not essential to practice the principles disclosed herein. In any case, the binary mask volume and the look-up table may be constructed such that they are sufficient to transform any existent voxel's coordinates to its fixed order index.

As used herein, voxel data may comprise any desired attributes for rendering each voxel, such as e.g., color, opacity, emittance, scalar magnitude, or partial derivatives of gradients. For each existent voxel, voxel data may be stored in the fixed order. Depending on the application, the 1D fixed order may be mapped to GPU storage directly via a buffer, or to elements in a 2D or 3D texture using a space-filling curve. In addition to, or alternatively, the voxel attributes themselves may be compressed in a 2D texture.

In the rendering stage 320, voxels may be rasterized in order of distance from the camera. The rasterization feature of the graphics processor may be exploited. According to the disclosed principles, and without loss of generality, front-to-back compositing with front-to-back view order may be implemented herein. The rendering stage is generally described as follows.

Indirect drawing may be enabled on the graphics processor. The number of vertices to draw may be supplied as the number of existent voxels. The vertex ID provided to the vertex program is interpreted as the voxel draw sequence number. Using one HistoPyramid traversal per vertex shader invocation, voxel draw sequence numbers may be transformed to 3D coordinates of the existent voxels as sorted in view order. The sorted voxels may be rasterized immediately by the graphics pipeline and then discarded. Because graphics hardware guarantees correct ordered blending of primitives according to their order of submission, this process may be sufficient for correct rendering in view order.

Figure 5:
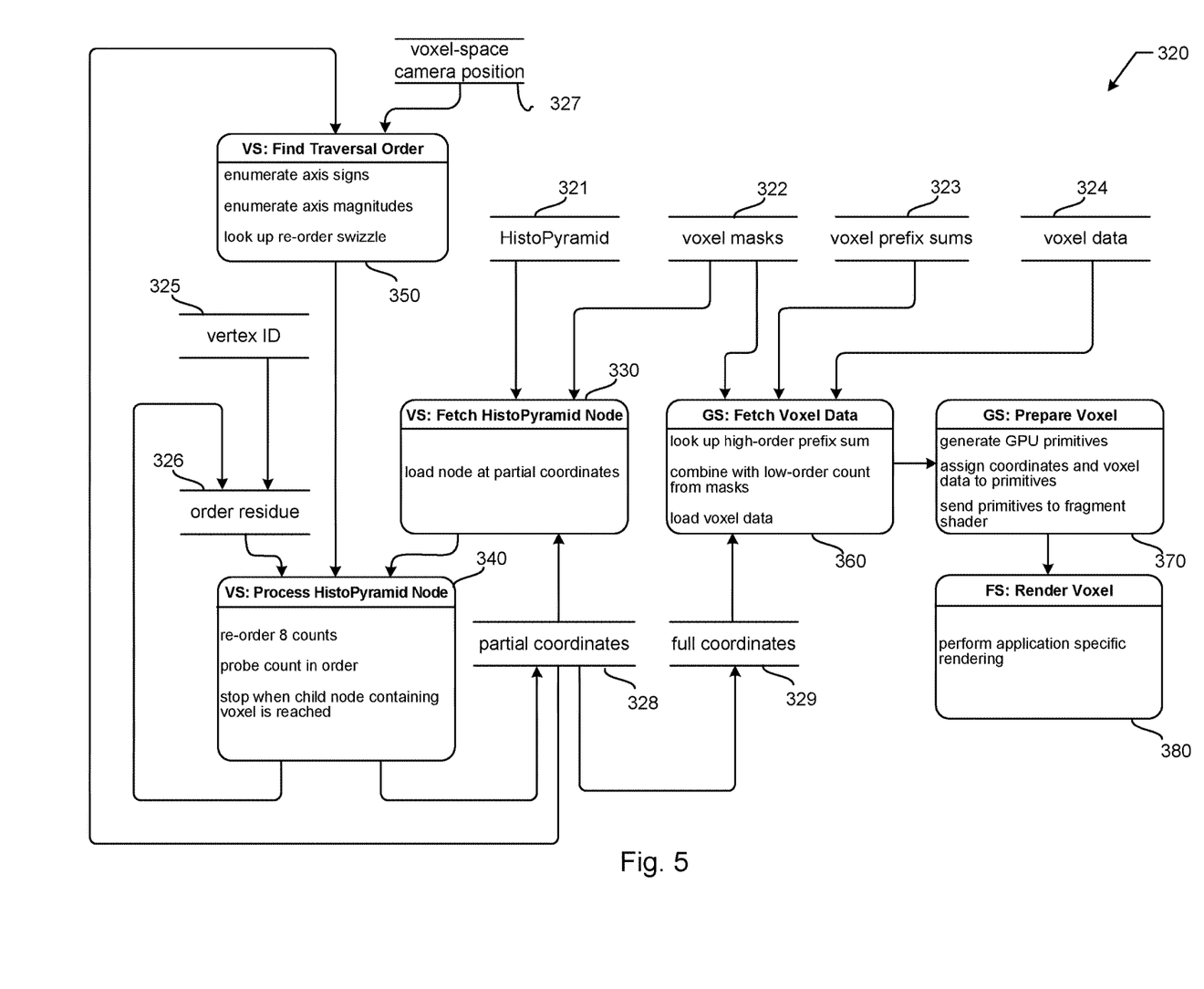
FIG. 5 illustrates details of a rendering stage used in the process illustrated in FIG. 4.

The rendering stage 320 may be implemented via a vertex shader (VS), geometry shader (GS), and fragment shader (FS). Details of the rendering stage 320 now follow with respect to FIG. 5. Specifically, FIG. 5 illustrates details of the rendering stage 320 that may be used in the process 300 illustrated in FIG. 4. The rendering stage is shown having six functional blocks 330, 340, 350, 360, 370, 380. Blocks 330, 340 and 350 may be implemented by the vertex shader (VS), blocks 360 and 370 may be implemented by the geometry shader (GS), and block 380 may be implemented by the fragment shader (FS). Inputs 321, 322, 323, 324, 325, 326, 327, 328 and 329 into the functional blocks 330, 340, 350, 360, 370, 380 are also shown in FIG. 5.

In the illustrated embodiment, the vertex shader (VS) implements block 330 to fetch the HistoPyramid node, block 340 to process the HistoPyramid node and block 350 to find the traversal order; the geometry shader (GS) implements block 360 to fetch voxel data and block 370 to prepare the voxel for rendering; and the fragment shader (FS) implements block 380 to render the voxel. This functionality is now described.

The vertex shader (VS) may fetch the HistoPyramid node (block 330) using a HistoPyramid input 321 and a voxel mask input 322. At block 330, a node may be loaded at partial coordinates input from the partial coordinates input 328. The loaded node at the partial coordinates may be input into block 340. Block 340 may also input the output of block 350 (traversal order) and an order residue from order residue input 326. In block 340, the vertex shader (VS), may re-order the eight counts of the node, probes each count in order, and may stop when the child node containing the voxel is reached. In block 350, the vertex shader (VS) may enumerate axis signs and magnitudes and look up a re-order swizzle using inputs such as the voxel-space camera position 327 and the partial coordinates 328.

For any view ray, exactly forty-eight traversal orders are possible per HistoPyramid node, due to the grid structure of the HistoPyramid. These orders may correspond to permutations of six axis orders multiplied by eight axis signs as described e.g., in Volumetric Sort. For each step of the HistoPyramid traversal (block 340), a traversal order may be determined (block 350), and used to rearrange the eight HistoPyramid node counts into an order of increasing distance with respect to the view ray. The linearized counts may then be probed until the ancestor node of the current voxel is found (block 340).

To determine the HistoPyramid node traversal order (block 350), the voxel-space camera position 327 may be subtracted from the bounding box center of the voxel-space HistoPyramid node. The resultant vector may be normalized. The signs and relative magnitudes of the normalized view vector's three components may be transformed into a discrete traversal order between 0 and 47.

For an orthographic projection, all view-rays are identical with respect to all HistoPyramid nodes. Only the voxel-space imaging plane normal may be needed to determine the traversal order, and this is constant per invocation of the vertex shader (VS). Therefore, upon every access to a HistoPyramid node, the node may be re-ordered in a constant manner. Such constant re-ordering may be achieved via a pre-compiled shader variant per traversal order, with the correct one selected just prior to rendering.

The voxel coordinates 329 may be passed from the vertex shader (VS) to the geometry shader (GS) and used at block 360 to fetch voxel data. Block 360 inputs voxel masks 322, voxel prefix sums 323 and voxel data 324 and may perform the following functions: looks up the high-order prefix sum, combines it with the low-order count from the masks and loads the appropriate voxel data. The output of functional block 360 is input into block 370, which may prepare the voxel for rendering. To do so, block 370 may generate GPU primitives, assigns coordinates and voxel data to the primitives and send the primitives to the fragment shader (FS).

To perform these functions, the fixed-order voxel index may be obtained via the sum of the value from the look-up table at the high-order bits of the voxel coordinates with the Hamming weight of preceding voxel existence bits from the low-order binary mask obtained during HistoPyramid traversal. The voxel data may then be fetched using the fixed-order index.

The fragment shader (FS) performs block 380, which is the rendering of the voxel. To do so, the fragment shader (FS) may perform application-specific rendering. For example, in one application, the voxel data may include scalar values for each of eight corners, and a volume rendering integral may be evaluated along the view ray passing through the fragment and the voxel. Correct ordered transparent composition may guaranteed based on the disclosed principles.

As discussed above, the execution of the rendering stage 320 may be split between vertex, geometry and fragment shaders. This may be done, in part, because it is necessary to access required GPU hardware functionality, such as primitive generation, throughout the stage 320. This splitting may also suit the GPU's internal load-balancing mechanisms. GPUs may be deeply pipelined and allow numerous vertex, geometry and fragment shader invocations all running simultaneously.

In implementation, some tasks may be placed in a different type of shader. For example, the geometry shader may perform the HistoPyramid traversal. This would not fundamentally alter the rendering stage 320. The described process 300 may use voxels as the parallel primitive for both voxel order determination and drawing. Existing splatting algorithms may use voxels as a primitive only for parallel or sequential drawing. The disclosed principles, however, may allow very broad data parallelism, highly coherent branches, and high data locality between nearby shader processing units. Furthermore, all data structures employed may be simple and compact enough to be fully re-generated at interactive rates. These are just some advantages of the disclosed embodiments.

Figure 6:
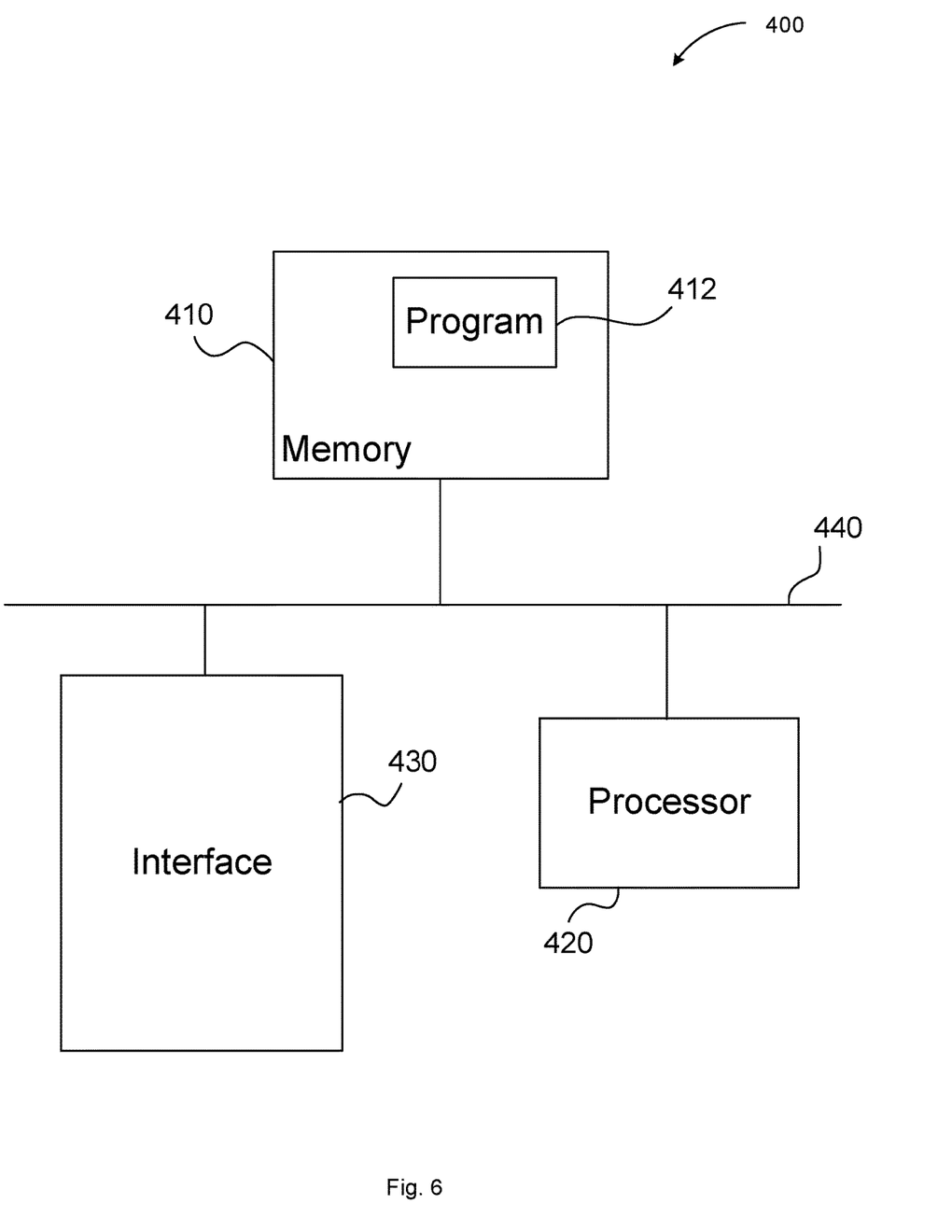
FIG. 6 illustrates an example configuration of a computer or computing device suitable for use in the workstations illustrated in FIGS. 1 and 2.

FIG. 6 generally illustrates certain components of a computing device 400 that may be utilized in the workstations 10, 110 to execute or that may embody components of the disclosed embodiments. For example, the computing device 400 device may include a memory 410, program instructions 412, one or more processors (e.g., processor and a graphics processor) 420 to execute instructions 412, one or more interfaces 430 (e.g., VR/AR interface) connected via one or more buses 440. The memory 410 may be or include one or more of cache, RAM, ROM, SRAM, DRAM, RDRAM, EEPROM and other types of volatile or non-volatile memory capable of storing data. The one or more processors 420 may be or include multiple processors, a single threaded processor, a multi-threaded processor, a multi-core processor, or other type of processor capable of processing data. It should be noted that one or more components of computing device 400 may be located remotely and accessed via a network. Accordingly, the system configuration provided in FIG. 6 is provided to generally illustrate how embodiments may be configured and implemented.

Method embodiments or certain steps thereof, some of which may be loaded on certain system components, computers or servers, and others of which may be loaded and executed on other system components, computers or servers, may also be embodied in, or readable from, a non-transitory, tangible medium or computer-readable medium or carrier, e.g., one or more of the fixed and/or removable data storage data devices and/or data communications devices connected to a computer. Carriers may be, for example, magnetic storage medium, optical storage medium and magneto-optical storage medium. Examples of carriers include, but are not limited to, a floppy diskette, a memory stick or a flash drive, CD-R, CD-RW, CD-ROM, DVD-R, DVD-RW, or other carrier now known or later developed capable of storing data. The processor 420 performs steps or executes program instructions 412 within memory 410 and/or embodied on the carrier to implement method embodiments.

From the foregoing, it will be appreciated that although specific examples have been described herein for purposes of illustration, various modifications may be made without deviating from the spirit or scope of this disclosure. It is therefore intended that the foregoing detailed description be regarded as illustrative rather than limiting, and that it be understood that it is the following claims, including all equivalents, that are intended to particularly point out and distinctly claim the claimed subject matter.

What is claimed is:

1. A workstation for volume visualization and interaction in a virtual reality or augmented reality environment, said workstation comprising:

a volume data input and processing unit adapted to input three-dimensional (3D) volume data from an input data source and process the 3D volume data;

a virtual or augmented reality interface adapted to receive user hand or head position and orientation data from one or more virtual reality or augmented reality devices;

a virtual or augmented reality interaction system coupled to the virtual or augmented reality interface, said virtual or augmented reality interaction system adapted to provide a plurality of interaction features for a user to interact with the 3D volume data and being adapted to output interaction data based on user interactions with the interaction features;

a graphics rendering unit adapted to receive the 3D volume data, user hand or head position and orientation data, and the interaction data, the graphics rendering unit adapted to render one or more of volume data on two-dimensional (2D) planes or in three-dimensional (3D) spaces via a plurality of graphics rendering mechanisms;

a volume editing system adapted to modify volume objects and surface representations of the volume objects in real-time, and being adapted to separate the volume objects and the surface representations into multiple independent segments; and a virtual scene management unit adapted to manage a virtual scene data structure which maintains the 3D volume data, the processed 3D volume data, an outcome of graphics rendering, and consequences of user interaction.

2. The workstation of claim 1, further comprising a haptic rendering unit adapted to interface with one or more haptic devices, the haptic rendering unit adapted to update the position and orientation of virtual tools from the one or more haptic devices to the virtual scene and to output volume force feedback to the one or more haptic devices.

3. The workstation of claim 1, wherein the 3D volume data comprises medical imaging of a plurality of modalities, including Computer Tomography (CT), CT Angiography (CTA), Cone Beam CT (CBCT), Magnetic Resonance Imaging (MRI), and MR Angiography (MRA).

4. The workstation of claim 1, wherein the plurality of interaction features comprises one or more of spatial tracking, manipulation, measurement, snapshot, visual configuration, cutaway and 2D overlay, drawing, hardware placement, laser pointer, multi-volume interaction, multi-user collaboration or undo-redo interaction features.

5. The workstation of claim 4, wherein the spatial tracking feature is adapted to identify the object in the virtual scene that the user interacts with and help with the execution of other interaction features.

6. The workstation of claim 4, wherein the manipulation feature is adapted to move, rotate, scale and interact with the rendered 3D volume objects.

7. The workstation of claim 4, wherein the measurement feature comprises quantifications of a distance between two points, a cumulative length of a polygonal chain, an angle between two lines, an angle between two planes, a circumference of a circle, a volume of a user defined space, or a volume within an iso-surface.

8. The workstation of claim 4, wherein the measurement feature further comprises a surface binding process adapted to optionally attach measurement points onto the surface close by.

9. The workstation of claim 4, wherein the cutaway and 2D overlay feature is adapted to reveal the internal structure of the 3D volume rendering, and being adapted to overlay a 2D volume rendering with the 3D rendering.

10. The workstation of claim 4, wherein the hardware placement feature is adapted to place one or more 3D objects in the virtual scene either as independent objects, or being mounted to any volume object in the virtual scene.

11. The workstation of claim 10, wherein the 3D objects comprise one or more models of medical implants, surgical plates, surgical screws or surgical instruments.

12. The workstation of claim 11, wherein the models of surgical plates may be automatically bent against the surface of one or more volume layers so it fits curvature of an anatomy structure.

13. The workstation of claim 10, wherein the 3D objects may be rendered with a color gradient representing a depth of intersection with one or more volume layers.

14. The workstation of claim 4, wherein the snapshot feature is adapted to capture a static picture of the virtual scene from a user specified perspective at a user defined time.

15. The workstation of claim 4, wherein the undo-redo feature is adapted to reverse the user interactions and recover the virtual scene, including the volume data and its surface representation, at a previous state; or reverse an undo operation and recover the virtual scene at the state prior to the undo operation.

16. The workstation of claim 1, wherein the processing of the 3D volume data comprises noise reduction, segmentation, coregistration of multiple 3D volume data, re-combination of distinct segmented volume objects, volume cropping, and topological smoothing.

17. The workstation of claim 1, wherein the volume data input and processing unit further comprises a volume-surface conversion process adapted to generate one or more surface models from the volume data, and being adapted to construct volume data based on the one or more surface models.

18. The workstation of claim 1, wherein the plurality of graphics rendering mechanisms comprises Shaded Surface Display (SSD), Volume Rendering Technique (VRT), Multi-Planar Reformation (MPR), Maximum Intensity Projection (MIP), and Minimum Intensity Projection (MinIP).

19. The workstation of claim 1, wherein one or more of the graphics rendering on 2D planes can be overlaid with the graphics rendering in 3D space.

20. The workstation of claim 1, wherein the graphics rendering can be constrained within one or more of user-specified regions of interest, and can be culled out by one or more of user-specified area.

21. The workstation of claim 1, wherein the graphics rendering unit further comprises an order-independent transparency rendering technique and architecture.

22. The workstation of claim 1, wherein the graphics rendering unit is adapted to stereographically render the virtual scene on a VR/AR display device, with a rendering perspective consistent with a physical position and orientation of the display device.

23. The workstation of claim 22, wherein the graphics rendering on an AR display device can be superimposed with a patient or physical object associated with the volume data.

24. The workstation of claim 1, wherein the graphics rendering unit is further adapted to render the virtual scene on a traditional 2D display, with a rendering perspective steadily following a headset orientation or otherwise specified by the user.

25. The workstation of claim 1, wherein the volume editing system comprises a volume cutting feature adapted to partition one or more volume objects and their surface representation by user defined regions, and being adapted to generate additional volume objects to represent newly cut partitions.

26. The workstation of claim 25, wherein the volume cutting feature further comprises a paint to separate mode adapted to define the cut regions by gradually painting on the volume objects by a virtual paint brush of various shapes and dimensions.

27. The workstation of claim 1, wherein the volume editing system further comprises a volume sculpting feature adapted to frequently modify the data of the volume objects and update their surface representation in regions specified by the user, and being adapted to gradually remove virtual materials from a represented geometry of the volume objects, or add virtual materials to it.

28. The workstation of claim 1, wherein the volume editing system further comprises a connected component labeling process adapted to detect the separation of the volume objects and their surface representation.

29. The workstation of claim 1, wherein the virtual scene management unit comprises a case exporting and importing process adapted to save the virtual scene of an active session, including the original, processed or edited volume objects, their surface representation, as well as the results of user interaction, as external files; and to load and recover the virtual scene from a previously saved session.

30. The workstation of claim 1, wherein the virtual scene management unit further comprises a model exporting process adapted to save the surface representation of the original, processed or edited volume data as polygon meshes.

31. The workstation of claim 1, wherein one or more of the volume data input and processing unit, virtual or augmented reality interface, virtual or augmented reality interaction system, graphics rendering unit, or virtual scene management unit are implemented by a graphic processing unit.

* * * * *